United States Patent [19]

Fischer

[11] Patent Number: 4,845,080
[45] Date of Patent: Jul. 4, 1989

[54] HUMAN CALCITONIN PEPTIDE WITH SALMON CALCITONIN-LIKE CHARACTERISTICS

[75] Inventor: Jan A. Fischer, Küsnacht ZH, Switzerland

[73] Assignee: Ciba-Geigy Corporation, Ardsley, N.Y.

[21] Appl. No.: 913,544

[22] Filed: Sep. 26, 1986

Related U.S. Application Data

[63] Continuation of Ser. No. 623,044, Jun. 21, 1984, abandoned.

[30] Foreign Application Priority Data

Jun. 27, 1983 [CH] Switzerland ............ 3496/83

[51] Int. Cl.$^4$ .............. A61K 37/30; C07K 7/36
[52] U.S. Cl. .................. 514/21; 514/808; 514/12; 424/95; 424/101; 530/307; 530/324; 530/417
[58] Field of Search .............. 424/101, 95; 514/21, 514/12, 808; 530/307, 324

[56] References Cited

FOREIGN PATENT DOCUMENTS 445115 12/1970 Australia .

OTHER PUBLICATIONS

Fischer et al., J. Clin. Endocrinol. Metab., vol. 57, No. 6, pp. 1314–1315, 1983.
Cano et al., J. Endocrinol., 92, 351–355, 1982.
Moukhtar, cited in Chem. Abstracts, vol. 79: 90371e, 1973.
Roos et al., Calcif. Tissue Res. 1977, 22 Suppl., pp. 298–302.
Maier, "Analogs of Human Calcitonin", cited in Chem. Abstracts, vol. 85, 137666w, 1976.
Roos et al., "Calcitonin Heterogeneity . . . " cited in Chem. Abstracts, vol. 87:181345f, 1977.
Perez Cano et al., "Identification of Both Human . . . " cited in Chem. Abstracts, vol. 96:214595d, 1982.
Tobler et al., "Identification and Characterization . . . " cited in Chem. Abstracts, vol. 99: 152664b, 1983.
C. R. Acad. Sc., vol. 276, Paris (6/73).
K. Lubke et al., Chemie und Biochemie der Aminosäuren, Peptide und Proteine I, Stuttgart (1975), p. 1984. Chem. Abstract 79:90371e (1973).
Tobler et al., Journal of Clinical Endocrinology & Metabolism, vol. 57, No. 4, (Oct. 1983), pp. 749–754.
Tobler, et al., Clinical Endocrinology, vol. 20, pp. 253–259, (1984).

Primary Examiner—Johnnie R. Brown
Assistant Examiner—Jacqueline M. Stone
Attorney, Agent, or Firm—Karl F. Jorda

[57] ABSTRACT

The invention relates to a substance from the calcitonin group, which substance can be isolated from the human body or can be obtained in a different manner, but clearly differs from the known human calcitonin-(1-32), the said substance having hypocalcaemic activity.

8 Claims, 1 Drawing Sheet

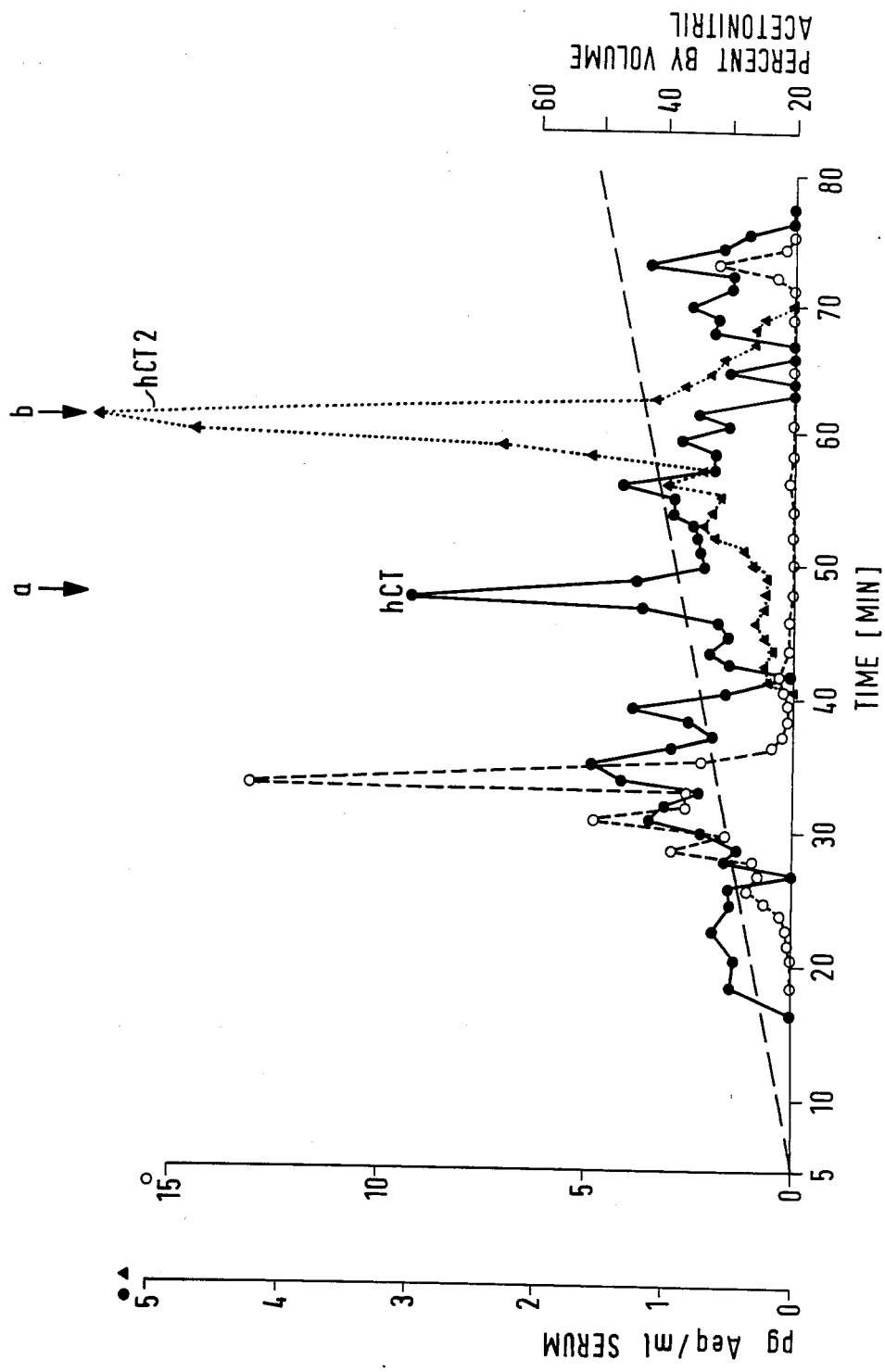

HUMAN CALCITONIN PEPTIDE WITH SALMON CALCITONIN-LIKE CHARACTERISTICS

This application is a continuation of application Ser. No. 623,044, filed June 21, 1984, now abandoned.

The invention relates to a substance from the calcitonin group and to salts thereof, to processes for producing them, to their use as medicaments and pharmaceutical preparations, which contain this substance together with a pharmaceutical carrier material.

The invention relates in particular to a substance from the calcitonin group, designated in the following also as calcitonin 2, abbreviated to hCT 2, which can be isolated from the human body or obtained in a different manner, having the following properties:

(a) capability to react with antibodies which do not recognise the human calcitonin-(1-32), abbreviated to hCT, having the formula

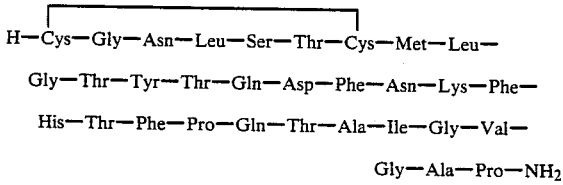

which belongs to prior art, but which can react with the salmon calcitonin-(1-32), abbreviated to sCT, having the formula

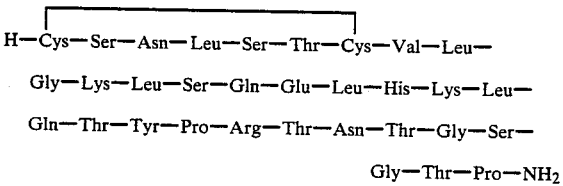

at up to a $10^5$-fold lower concentration;

(b) retention time not distinguishable from that of the synthetically produced sCT in the following high-performance liquid chromatographic system (HPLC-system):

adsorbent: Nucleosil 10 $C_{18}$ ® or a different adsorbent having comparable properties, 250 mm long column, 4.6 mm in diameter, charging with 1 ng to 20 μg, preferably 1-10 ng, of hCT 2, linear gradient consisting of the solutions A (0.1 molar aqueous heptafluorobutyric acid) and 25-73 percent by volume of B (20 percent by volume of the solution A and 80 percent by volume of acetonitrile), corresponding to 20-58 percent by volume of acetonitrile, during 90 minutes at a flow rate of 1.5 ml/minute;

(c) in the human serum no initiation of the formation of detectable amounts of antibodies which are able to react with sCT, the binding to [$^{125}$I]sCT having a specific activity of 600 Ci/mmol being used for verfying this evidence;

and the invention relates also to the salts of hCT 2.

The absorbent designated as Nucleosil 10 $C_{18}$ in the HPLC system consists of silica gel to which are bound actadecyl groups by way of Si-C bonds. The silica gel is in the form of through and through porous, spherical particles having a particle size of $10\pm1.5$ μm, a mean pore diameter of 100 Å, a pore volume of 1.0 ml/g and a specific surface area (BET) of 300 m²/g, which are stable to pressure up to 600 bar, Nucleosil 10 $C_{18}$ is supplied by Macherey Nagel, Werkstrasse 6-8, Postfach 307, D-5160 Düren.

The invention relates in particular to the above-mentioned substance of which the elution volume in the following gel permeation chromatographic system (gel system) is indistinguishable from that of the synthetically produced sCT:

Gel: Bio-Gel P-150 ® (100-200 mesh) or a different gel with comparable properties, 100 cm long column having a diameter of 1.6 cm, charging with 1 ng to 10 ng of hCT 2, eluant consisting of ammonium acetate (0.2 mol/l, ph 4.6) and bovine serum albumin (0.5 mg/ml), during 48 hours at a flow rate of 5 ml/hour.

The absorbent designated as Bio-Gel ® in the gel system consists of porous polyacrylamide particles having a diameter in the hydrogenated condition of 80-150 μm. Bio-Gel P-150 ® is supplied by Bio-Rad, Chemical Division, 2200 Wright Avenue, Richmond, CA 94804, USA.

The substance, hCT 2, according to the invention is present at low concentration for example in the human brain, in the human thyroid gland, in the human hypophysis and in the human blood plasma and blood serum.

The invention relates principally to the aforementioned substance according to the present invention and to the salts thereof, outside a living organism and at a concentration which is enriched compared with the natural occurrence, primarily to hCT 2 in an essentially pure form or together with added pharmaceutical carrier materials.

The substance hCT 2 differs from the known hCT in the aforementioned HPLC system by virtue of a clearly different retention time; on the other hand, hCT 2 has a retention time practically identical to that of sCT. In the aforementioned gel system, the elution volume of hCT 2 differs from that of hCT, but is practically identical to that of sCT. These facts indicate that hCT 2 with respect to the amino acid composition, even though not necessarily with respect to the amino acid sequence, is more closely related to sCT than to hCT. With regard to immunology, however, hCT 2 differs greatly from sCT. Whereas sCT as foreign peptide produces in the human serum an antibody response, there are formed no antibodies specific for sCT as a response to the presence of hCT 2 in the human serum, as can be verified with the radioimmunoassay (RIA).

It may be assumed that there are produced no antibodies at all, neither those specifically for sCT nor others, against hCT 2 in the human serum, since hCT 2 has an endogenous substance is probably not recognised as being immunologically foreign.

According to the findings hitherto, hCT 2 is only one chemical compound. Theoretically, however, there is a possibility that hCT 2 is a mixture of novel calcitonins, the individual components of which cannot be visibly separated in the aforementioned HPLC- and gel systems. In the latter case, the invention relates both to the mixture and to each individual component of the mixture. The individual components can be separated in the customary manner, for example by chromatography in further suitable HPLC- or gel systems, or can be produced separately by known methods of peptide chemistry, either synthetically or by genetic engineering. The structural clarification of the individual components, necessary beforehand for the synthesis, can also be performed on the mixture.

The present invention relates also to the salts, particularly to the acid addition salts, of hCT 2, above all to pharmaceutically applicable nontoxic salts with acids, for example with inorganic acids, especially mineral acids, for example hydrochloric acid, sulfuric acid or phosphoric acid, or to salts with organic carboxylic, sulfonic or sulfo acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isopicotinic acid; also amino acids, as well as methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid, or with other acidic organic compounds, such as ascorbic acid.

It is possible to use for isolation or purification also pharmaceutically unsuitable salts. For therapeutic application, however, only the pharmaceutically applicable nontoxic salts are used, which are therefore preferred.

hCT 2 has a hypocalcaemic action, that is to say, it lowers the calcium and phosphate levels in the blood, and protects the bones from mineral loss, and can be used therefore as a medicament, especially for the same indications as hCT, for example the commercially available Cibacalcin ®, for example in the case of bone metabolism disturbances, such as osteoporosis or Morbus Paget.

The doses of hCT 2 to be administered to warm-blooded animals, particularly to man, of about 70 kg body weight are about 5 µg to about 50 µg, for example about 20 µg, per day. Administration is carried out preferably parenterally, for example on 5 days in the week during about 3 months.

hCT 2 also exhibits effects on the central nervous system. As can be determined by receptor-autoradiography, there are binding sites for hCT 2 in the human brain. Furthermore, since the concentration of hCT 2 in the brain is similar to that of hCT, whereas in the thyroid gland hCT occurs at a concentration approximately 200 times greater than that of hCT 2, the action of hCT 2 on the central nervous system is of greater importance than are the known functions of hCT in the nervous system.

hCT 2 is obtained for example by centrifuging human blood serum at 4° C. and at 48,000×g for 30 minutes; adsorbing the supernatant to octadecasilyl silica gel cartridges, preferably octadecasilyl silica gel Sep-Pak $C_{18}$ cartridges (Waters Assoc., Milford, Mass.), in 0.1% aqueous trifluoroacetic acid; eluting hCT 2 from the cartridges with 60% (v/v) aqueous acetonitrile containing 0.1% of trifluoroacetic acid; lyophilising the eluate; treating the lyophilisate with 0.1 molar acetic acid; centrifuging the dissolved part at 4° C. and at 48,000×g for 30 minutes; chromatographing the clear supernatant in the aforementioned HPLC system; and isolating hCT 2 from the corresponding fractions.

hCT 2 is obtained also by, in chronological sequence, firstly adding to frozen human hypophyses the 10- to 20-fold volume of ice-cold, aqueous 2 molar acetic acid, heating for 5 minutes in a boiling water-bath, pulverising the hypophyses with an Ultra-Turrax (18K homogeniser, Ika-Werke, Staufen, Germany) or with a device comparable with regard to the effect to be obtained, freezing the homogenates at 31 20° C. for about 12 hours, thawing them at room temperature, freezing them again, thawing them again, centrifuging them at 48,000 g and at 4° C. for 30 minutes, adsorbing the clear supernatant, as described above, onto octadecasilyl silica gel cartridges, chromatographing in the above-mentioned HPLC- and/or gel-system, and isolating hCT 2 from the corresponding fractions.

For the purpose of detecting the fraction(s) containing the hCT 2, there is used a radioimmunoassay ([$^{125}I$] sCT with the specific acitivity of 500 Ci/mmol, antibodies to synthetic sCT, as standard synthetic sCT).

The invention relates in particular to the hCT 2 or a salt thereof obtainable according to the isolation process described in the foregoing and in the Examples.

The salts of hCT 2 can be produced in a manner known per se. Acid addition salts are obtained for example by treatment with a suitable acid, for example one of the acids mentioned above, or with a suitable anion-exchange reagent.

Salts can be converted in the customary manner into the free compounds; acid addition salts for example by treatment with a suitable basic agent.

The invention relates also to pharmaceutical preparations which contain as active ingredient an effective dose of hCT 2 or of a salt thereof, together with a significant amount of a pharmaceutical carrier material, especially to those preparations for intranasal or parenteral administration, such as intramuscular or intravenous administration, to warm-blooded animals, such as in particular to humans.

The dosage of active ingredient depends on the species of warm-blooded animal, on the body weight, age and individual condition, and on the disease to be treated as well as on the mode of administration.

The novel pharmaceutical preparations for parenteral administration contain in the ready-for-use form from about 0.001 per mil by weight to about 1 percent by weight, preferably from about 0.005 per mil by weight to about 0.1 per mil by weight, for example 0.01 per mil by weight, of active ingredient. The pharmaceutical preparations according to the invention can be for example in the form of dosage units, such as ampoules.

There are preferably used solutions of the active ingredient, in addition suspensions, especially isotonic aqueous solutions or suspensions; and these, for example in the case of lyophilised preparations which contain the active ingredient alone or together with a carrier, for example mannitol, can be produced before use. Suspensions in oil in particular are especially suitable for intranasal administration. The pharmaceutical preparations can be sterilised and/or can contain auxiliaries, for example preservatives, stabilisers, wetting and/or emulsifying agents, solubilisers, salts for regulating the osmotic pressure and/or buffers; and they are produced in a manner known per se, for example by means of conventional dissolving or lyophilising processes. The stated solutions or suspensions can contain substances increasing visocity, such as sodium carboxymethyl cellulose, carboxymethyl cellulose, dextran, polyvinyl pyrrolidone or preferably gelatin.

Suspensions in oil contain as the oily component the vegetable, synthetic or semisynthetic oils customarily used for injection purposes. To be mentioned as such are in particular liquid fatty acid esters which contain, as the acid component, a long-chain fatty acid having 8-22, especially 12-22, carbon atoms, for example lauric acid, tridecylic acid, myristinic acid, pentadecylic acid, palmitic acid, margarinic acid, stearic acid, arachic acid, behenolic acid or corresponding unsaturated acids, for example oliec acid, elaidic acid, erucic acid, brassidic acid or linoleic acid. The alcohol component has a maximum of 6 carbon atoms and is mono- to polyhydric, for example mono- di- or trihydric alcohol, for example methanol, ethanol, propanol, butanol or pentanol, or isomers thereof, especially however glycol or glycerol. Fatty acid esters to be mentioned therefore are for example: ethyl oleate, isopropyl myristate, isopropyl palmitate, "Labrafil M 2735" (polyoxyethylene glycerol trioleate, Gattefossé, Paris), "Miglyol 812" (triglyceride of saturated fatty acids of chain-length $C_8$ to $C_{12}$, Chemische Werke Witten/Ruhr, Germany), particularly vegetable oils, such as cottonseed oil, almond oil, olive oil, castor oil, sesame oil or soybean oil, especially peanut oil.

The injection preparations are produced in the usual manner under antimicrobial conditions, likewise the filling into ampoules or vials as well as the sealing of the containers.

The following Examples illustrate the invention. Temperatures are given in degrees Centigrade.

EXAMPLE 1

Extraction of hCT 2 from human plasma, and purification by means of high-performance liquid chromatography Venous blood of normal persons is withdrawn in heparinised vacutainers (Becton Dickinson France SA, Grenoble, F); subsequently centrifuged twice for 10 minutes at 4° C. and at $1700 \times g$ (centrifuge: Superspeed RC-2B, Sorvall, Du Pont Instruments, Newton, Conn., USA); and the supernatants are combined, and frozen at $-20°$ C. The plasma is thawed within 2 weeks and centrifuged for 30 minutes at 4° C. at $48,000 \times g$ (fixed-angle rotor ["Festwinkelrotor"]: Sorvall SS-34, polyethylene tubes: Du Pont Instruments, Newton, Conn., USA). The combined supernatants (minimum of 20 ml) are extracted at 4° C. portionwise (3–5 ml), using the following method, by adsorption onto octadecasilyl silica gel (Sep-Pak $C_{18}$ cartridges, Waters Assoc., Milford, Mass., USA).

Extraction

Before application of the plasma specimen, the Sep-Pak cartridge is fixed onto a 10 ml disposable syringe (Henke-Sass Wolf GmbH, Fed. Repub. of Germany) with a Luer-lock connection, and wetted with 5 ml of methanol (Merck AG, Darmstadt, Fed. Repub. of Germany), followed by 10 ml of 0.1% trifluoroacetic acid (TFA, sequencer grade, Rathburn Chemicals, Walkerburn, GB) in aqua bidest. (v/v). A second 10 ml disposable syringe with mounted piston is subsequently fixed onto the cartridge; 3–5 ml of plasma are then filled into the first syringe and slowly pressed into the second syringe, without air penetrating into the cartridge. After a to and fro pressing of the plasma five times, one syringe is removed, the plasma is pressed through for a final time and discarded. The cartridge is thereupon washed with 10 ml of 0.1% TFA, and is finally eluted with 3 ml of 60% acetonitrile/0.1% TFA (v/v) dropwise into a plastics scintivial (Packard Inst. Company, Downers Grove, Ill., USA). Five eluates are combined in a container; they are then slantingly frozen in liquid nitrogen and lyophilised. After lyophilisation, the extract obtained is dissolved in 1 ml each of 60% acetonitrile/0.1% TFA. In the case of extractions of more than 25 ml of plasma, several extracts are combined in a scintivial. The empty vials are rinsed with the same amount of solvent, and the rinsing liquid is added to the combined extracts, frozen and again lyophilised. This lyophilisate is dissolved in 2 ml of 0.1M acetic acid (Merck), centrifuged at 4° C. at $48,000 \times g$ for 20 minutes in a polycarbonate tube, and the supernatant is subsequently separated by means of reverse-phase high-performance liquid chromatography (HPLC).

HPLC

The HPLC analyses are carried out at room temperature. The equipment consists of two pumps (Model 110A, Altex, Berkeley, Calif., USA), a high-pressure gradient mixing chamber (Altex Model 400), as well as a microprocessor/programmer (Altex Model 420) as control unit. The samples are applied manually by means of a non-septate injector provided with a 2 ml sample feeding loop (Model RE 7125, Rheodyne Inc., Berkeley, Calif., USA). The columns used are stainless steel columns (25 cm long, 4.6 mm internal diameter, Altex) filled according to the slurry technique from top to bottom with Nucleosil $10\mu$ $C_{18}$ (Macherey Nagel, Düren, Fed. Repub. of Germany). Solution A consists of 0.1M aqueous heptafluorobutyric acid (sequencer grade, Rathburn Chemicals), which has been additionally pressed through a wetted Sep-Pak-$C_{18}$ cartridge. Solution B consists of 20% of solution A and 80% of acetonitrile (HPLC grade S, Rathburn Chemicals) (v/v). The solutions are gassed before the analysis for 2 minutes with helium, and the column is equilibrated for about one hour with 75% of solution A and 25% of solution B at a flow rate of 1.5 ml/minute. After a charging phase of 2.5 minutes under the initial conditions (25% of solution B, contains 20% of acetonitrile) the peptides are eluted, with a linear gradient of 25% to 73% of the solution B (20–58% of acetonitrile) for 90 minutes with a flow rate of 1.5 ml/minute. Eluent fractions of about 1.5 ml (95 fractions in 100 minutes) are collected, after passage through a UV detector (Uvikon LCD 725, with variable wavelength, adjusted to 254 nm, full-scale reading at 0.05 to 0.1 absorption units, recording by means of a W+W recorder Tarkon 600, both from Kontron AG, Zürich, CH) and through the motorised valve (Altex Model 402, with change-over switching either to waste or to fraction collector), in a synchronised fraction collector (Buchler Alpha 200, Kontron AG), in siliconised glass tubes. To avoid a possible adsorption of the peptides on the glass wall, 300 $\mu$l of a solution of 1% of bovine serum albumin (Behring Werke, Marburg-Lahn, Fed. Repub. of Germany) and 0.05% of sodium azide (Fluka AG, Buchs, CH) (w/v) in 0.1M acetic acid are introduced before the analysis into each tube. The fractions are mixed on a Vortex mixer (Scientific Industries Inc., Springfield, Mass., USA), frozen at $-20°$ C. and lyophilised. Before the radioimmunological determination of the calcitonin concentration, described below, 0.5 ml of 0.01M acetic acid is placed into each tube and mixed.

The recovery rate of synthetic human calcitonin-(1-32), which has been added before extraction to the plasma, is 40 to 70% according to the HPLC.

After each HPLC run, column and sample loop are regenerated successively with 15 ml of solution B, 150 ml of 90% methanol/1% TFA, 40 ml of butanol-1 and 140 ml of methanol, under which the column is kept.

Measuring method (radioimmunological determination of the calcitonin concentration)

The concentration of hCT 2 is determined radioimmunologically in a concentration series. 10, 20, 50 and 100 μl, respectively, of the HPLC fractions, which have been aftertreated as described above, are preincubated for 3 days at 4° C. together with 100 μl of antibody serum to synthetic sCT (Sandoz AG, Basle, Switzerland) in an immunoassay buffer with a total volume of 300 μl (immunoassay buffer: 0.05M phosphate, pH 7.5, 10% of human serum containing no detectable amounts of immunoreactive sCT), and, after the addition of 200 μl of assay buffer having 15,000 dpm of [$^{125}$I]sCT (specific activity 600 Ci/mmol), subsequently incubated for a further 3 days at 4° C. The labelling of sCT with $^{125}$I is performed with Chloramin-T (Eastman Kodak, Rochester, USA) essentially according to the method of W. M. Hunter and F. C. Greenwood (Nature [London] 194, 495–496 [1962]. With the final dilution of the antibodies (1:25,000), 30 to 40% of the antibodies are bound to the [$^{125}$I]sCT, that is to say, the specific binding is 30–40%. The standard used is the same synthetic sCT; a half maximum inhibition of the binding of [$^{125}$I]sCT to the antibodies occurs with about 100 pg of sCT (=0.03 pmol). A comparable inhibition of the binding is not obtained by 10 μg of hCT.

The above-mentioned antibody serum is obtained as follows: The antibodies are produced in a 25 kg goat after primary immunisation with 200 μg of sCT (see above) as antigen, and reimmunisation with 100 μg of the same antigen 30 days after the primary immunisation. For immunisation, sCT is dissolved in 0.01M acetic acid (1 mg/ml), the solution is mixed with 2 percent by weight of solid aluminium hydroxide (Alhydrogel, Superfos Export Co. a/s Copenhagen, Denmark) and the mixture is suspended in an equal volume of complete Freund's adjuvant (Difco Laboratories, Detroit, Mich., USA). This suspension is produced in an Omnimixer (Sorvall) at 4° C. at the maximum mixing rate. 0.5–1.0 ml of suspension is drawn up into disposable syringes (Primo 1 ml, Asik I/S, Denmark), and administered on each leg subcutaneously in the region of the subaxillary lymph nodes. Ten days after the abovementioned reimmunisation, 50–80 ml of blood containing the desired antibodies against sCT are withdrawn from the jugular vein into heparinised tubes, and the plasma obtained is stored at −20° C. in 3–5 ml portions.

The quantity of antibodies obtained is estimated by measurement of the binding of the withdrawn plasma to [$^{125}$I] sCT. Antibody-bound and free [$^{125}$I]sCT are separated by means of charcoal coated with dextran, in the main according to the method of V. Herbert, K.-S. Lau, C. W. Gottlieb and S. J. Bleicher [J. Clin. Endocrinol. Metab. 25, 1375–1384 (1965)]. The same method is used for the detection of antibodies in human serum.

BRIEF DESCRIPTION OF THE DRAWING

FIG. 1 is a chromatography profile of an HPLC separation.

DETAILED DESCRIPTION OF THE DRAWING

Chromatography profile

The chromatography profile of the HPLC separation described in Example 1 above is illustrated in FIG. 1. The concentration is plotted on the ordinate, given in picogram equivalents, different scales applying for the curves marked with ● and ▲ on the one side and with o on the other side.

The time which has passed since commencement of elution is plotted on the abscissa. The broken straight-line gives the composition of the linear gradient used for the elution by indication of the acetonitrile content. The arrows marked with a or b denote the positions of the elution of hCT and sCT, respectively.

For the determination of the concentration values given in FIG. 1, there is used for each of the three curves labelled with filled-in circles "●", triangles "▲" or blank circles " o " a different radioimmunoassay (different antibodies), namely: for the concentration values marked with filled-in circles an RIA against synthetic hCT (cf. F. M. Dietrich, W. H. Hunziker and J. A. Fischer, Acta Endocrinologica 80 [1975] 465–486); for the concentration values marked with triangles the above-described RIA against synthetic sCT; and for the concentration values marked with blank circles, which are of less interest within the scope of this Application, an RIA against human PDN-21. Synthetically produced PDN-21, a peptide having 21 amino acids, is described by MacIntyre et al., Nature (London) 300, 460–462.

EXAMPLE 2

Gelatin solution

An aqueous solution of hCT 2 sterilised by filtration is mixed, with heating, with a sterile gelatin solution, which contains phenol as a preservative, under aseptic conditions, so that 1.0 ml of solution has the following composition:

hCT 2: 10 μg
gelatin: 150.0 mg
phenol: 4.7 mg
dist. water up to: 1.0 ml

The mixture is filled aseptically into 1.0 ml phials.

EXAMPLE 3

Sterile dry substance for injection

5 μg of hCT 2 are dissolved in 1 ml of an aqueous solution with 20 mg of mannitol. The solution is sterilised by filtration and is then filled, under aseptic conditions, into a 2 ml ampoule; it is subsequently frozen and lyophilised. The lyophilisate before use is dissolved in 1 ml of distilled water or in 1 ml of physiologic salt solution. The solution is administered intramuscularly or intraveneously. This formulation can also be filled into double-chamber injection ampoules.

EXAMPLE 4

Nasal spray

200 μg of finely ground (<5.0μ) hCT 2 are suspended in a mixture of 3.5 ml of "Miglyol 812" and 0.08 g of benzyl alcohol. This suspension is filled into a container with a dosing valve. There are then injected 5.0 ml of "Freon 12" under pressure through the valve into the container. The "Freon" is dissolved in the miglyol/benzyl alcohol mixture by shaking. This spray container contains about 100 single doses, which can be administered individually.

EXAMPLE 5

Extraction of hCT 2 from human hypophyses and purification with gel filtration 5–10 hypophyses (3–5 g) of patients without disorders of endocrine glands or of the skeleton are removed during autopsy not later than 20 hours after the occurrence of death, and stored at −80° C. for no longer than 3 weeks.

Extraction

To the frozen hypophyses is added the 10-fold volume of ice-cold, aqueous 2 molar acetic acid, and the sample is introduced for 5 minutes into a boiling waterbath. The hypophyses are then pulverised with an Ultra-Turrax (18K homogeniser, Ika-Werke, Staufen, Fed. Repub. of Germany). The homogenates are frozen for about 12 hours at −20° C., subsequently thawed at room temperature, again frozen and again thawed and finally centrifuged at 48,000 g at 4° C. for 30 minutes. The clear supernatant is lyophilised and afterwards stored at −20° C.

The supernatant is drawn up into a 10 ml disposable syringe and extracted with a Sep-Pak cartridge as in Example 1.

Gel filtration (gel system)

The gel filtration analysis is performed at 4°–6° C. The apparatus consists of a pump (Model PMP-10, Ismatec SA, Zürich, Switzerland) and a chromatography column of plastics material (100 cm long, 1.6 cm internal diameter, Pharmacia Fine Chemicals AB, Box 175, S-751 04, Uppsala 1, Sweden). The elution solution comprises 0.2 mol/l of ammonium acetate (E. Merck, Darmstadt, Fed. Repub. of Germany) having the pH value of 4.6, and 0.05% of bovine serum albumin (Behring Werke, Marburg [Lahn], Fed. Repub. of Germany). The column is equilibrated with the solution for about 72 hours. The solution (2 ml) is adsorbed through a three-way cock within about 30 minutes. The peptides are eluted for 48 hours at a flow rate of 5.0 ml/hour. The eluent fractions of about 2.5 ml (100 fractions in 48 hours) are collected in a fraction collector (LKB 7000 Ultrorac, Bromma, Sweden). The fractions are frozen at −20° C. and lyophilised. Before the radioimmunological determination of the calcitonin concentration, 0.5 ml of 0.01 molar aqueous acetic acid is placed into each tube and mixed. The recovery rate of synthetic hCT, which has been added before extraction to the hypophysis extract, amounts after gel filtration to 40 to 80%.

What is claimed is:

1. Human calcitonin 2, which is a human calcitonin peptide, or mixture of peptides, substantially free from human calcitonin-(1-32), having the formula

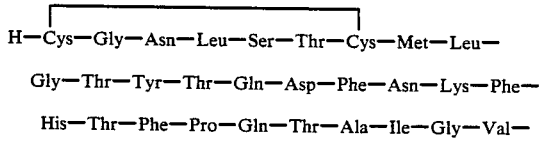

in a concentration at least substantially enriched compared with the highest concentration of said human calcitonin 2 naturally occurring in the human body, having the following properties:

(a) the capability to react with goat serum antibodies which do not recognize human calcitonin-(1-32), at a concentration at which human calcintonin 2 is already able to react with said antibodies, but which react with salmon calcitonin-(1-32) having the formula

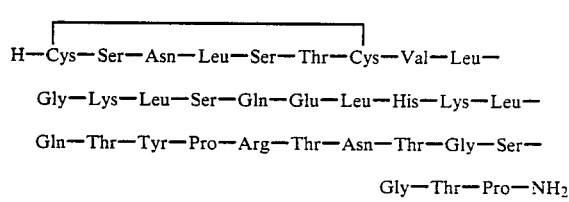

at up to a $10^5$-fold lower concentration than with human calcitonin-(1-32);

(b) a retention time substantially identical to that of synthetic salmon calcitonin-(1-32) in high-performance liquid chromatography, using as adsorbent, an adsorbent consisting of silica gel, to which are bound octadecyl groups by way of Si-C bonds, in the form of porous, spherical particles having a particle size of 10±1.5 μm, a mean pore diameter of 100 Å, a pore volume of 1.0 ml/g and a specific surface area of 300 m²/g and being stable to pressures up to 600 bar, in a 250 mm long column having a diameter of 4.6 mm, being charged with 1 ng to 20 μg of said human calcitonin 2, in a linear gradient consisting of solution A, being 0.1 molar aqueous heptafluorobutyric acid, and 25–73 percent by volume of solution B, being 20 percent by volume of solution A and 80 percent by volume of acetonitrile, corresponding to 20–58 percent by volume of acetonitrile, for 90 minutes at a flow rate of 1.5 ml/minute; and (c) in human serum, no initiation of the formation of detectable amounts, as compared to salmon calcitonin-(1-32), of antibodies which are able to react with salmon calcitonin-(1-32) based upon antibody binding to [$^{125}$I] salmon calcitonin-(1-32) having a specific activity of 600 Ci/mmol; and pharmaceutically acceptable salts thereof.

2. Human calcitonin 2 according to claim 1, wherein in (b) said absorbent is charged with 1–10 ng of human calcitonin 2.

3. Human calcitonin 2 according to claim 1, wherein the said human calcitonin 2 is indistinguishable from synthetic salmon calcitonin-(1-32) in terms of elution volume in gel permeation chromatography, wherein said gel consists of porous polycrylamide particles having a diameter in the hydrated state of 80–150 μm, in a 100 cm long column having a diameter of 1.6 cm, charged with 1 ng to 10 ng of said human calcitonin 2, wherein the eluant consists of ammonium acetate solution present in a concentration of 0.2 mol/liter and a pH of 4.6 and bovine serum albumin in a concentration of 0.5 mg./ml, during 48 hours at a flow rate of 5 ml/hour.

4. Human calcitonin 2 according to claim 1 in substantially pure form.

5. A pharmaceutical composition containing an effective hypocalaemic amount of human calcitonin 2 or a pharmaceutically acceptable salt thereof and a pharmaceutically acceptable carrier; said human calcitonin 2 being a human calcitonin peptide, or mixture of peptides, in a concentration at least substantially enriched compared with the highest concentration of said human calcitonin 2 naturally occuring in the human body, having the following properties:
  (a) the capability to react with goat serum antibodies which do not recognize human calcitonin-(1-32), having the formula

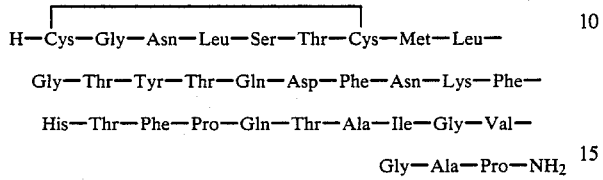

but which react with salmon calcitonin-(1-32) having the formula

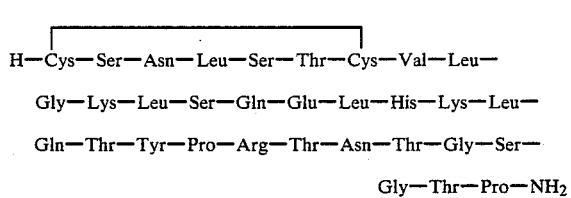

at up to a $10^5$-fold lower concentration;
  (b) a retention time substantially identical to that of synthetic salmon calcitonin-(1-32) in high-performance liquid chromtography, using as adsorbent, an adsorbent consisting of silica gel, to which are bound octadecyl groups by way of Si-C bonds, in the form of porous, spherical particles having a particle size of $10\pm1.5$ μm, a mean pore diameter of 100 Å, a pore volume of 1.0 ml/g and a specific surface area of 300 m²/g and stable to pressures up to 600 bar, in a 250 mm long column having a diameter of 4.6 mm, being charged with 1 ng to 20 μg of said human calcitonin 2, in a linear gradient consisting of solution A, being 0.1 molar aqueous heptafluorobutyric acid, and 25-73 percent by volume of solution B, being 20 percent by volume of solution A and 80 percent by volume of acetonitrile, corresponding to 20-58 percent by volume of acetonitrile, for 90 minutes at a flow rate of 1.5 ml/minute; and
  (c) in human serum, no initiation of the formation of detectable amounts, as compared to salmon calcitonin-(1-32), of antibodies which are able to react with salmon calcitonin-(1-32) based upon antibody binding to [$^{125}$I] salmon calcitonin-(1-32) having a specific activity of 600 Ci/mmol.

6. A method of lowering calcium and phosphate levels in the blood of a warm blooded animal in need thereof, comprising intranasally or parenterally administering to said mammal a hypocalcaemically effective amount of human calcitonin 2 or a pharmaceutically acceptable salt thereof; said human calcitonin 2 being a human calcitonin peptide, or mixture of peptides, in a concentration at least substantially enriched compared with the highest concentration of said human calcitonin 2 naturally occuring in the human body, having the following properties:
  (a) the capability to react with goat serum antibodies which do not recognize human calcitonin-(1-32), having the formula

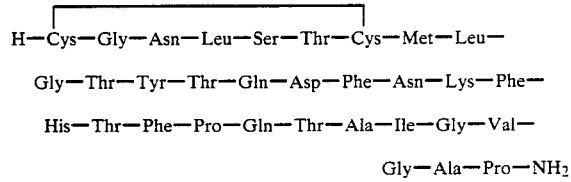

but which react with salmon calcitonin-(1-32) having the formula

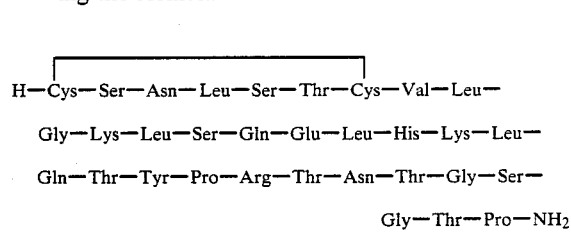

at up to a $10^5$-fold lower concentration;
  (b) a retention time substantially identical to that of synthetic salmon calcitonin-(1-32) in high-performance liquid chromatography, using as adsorbent, an adsorbent consisting of silica gel, to which are bound octadecyl groups by way of Si-C bonds, in the form of porous, spherical particles having a particle size of $10\pm1.5$ μm, a mean pore diameter of 100 Å, a pore volume of 1.0 ml/g and a specific surface area of 300 m²/g and stable to pressures up to 600 bar, in a 250 mm long column having a diameter of 4.6 mm, being charged with 1 ng to 20 μg of said human calcitonin 2, in a linear gradient consisting of solution A, being 0.1 molar aqueous heptafluorobutyric acid, and 25-73 percent by volume of solution B, being 20 percent by volume of solution A and 80 percent by volume of acetonitrile, corresponding to 20-58 percent by volume of acetonitrile, for 90 minutes at a flow rate of 1.5 ml/minute; and
  (c) in human serum, no initiation of the formation of detectable amounts, as compared to salmon calcitonin-(1-32), of antibodies which are able to react with salmon calcitonin-(1-32) based upon antibody binding to [$^{125}$I] salmon calcitonin-(1-32) having a specific activity of 600 Ci/mmol.

7. The composition of claim 5 which is substantially free of said human calcitonin-(1-32).

8. The method of claim 6 wherein said administration of said human calcitonin 2 is administered substantially free of said human calcitonin-(1-32).

* * * * *